(12) United States Patent
Schatz

(10) Patent No.: US 6,196,841 B1
(45) Date of Patent: Mar. 6, 2001

(54) FILTER FOR SPRAY DUCTS OF DENTAL OR SURGICAL HANDPIECES

(75) Inventor: Norbert Schatz, Bürmoos (AT)

(73) Assignee: Dentalwerk Bürmoos Gesellschaft m.b.H., Bürmoos (AT)

( * ) Notice: Subject to any disclaimer, the term of this patent is extended or adjusted under 35 U.S.C. 154(b) by 0 days.

(21) Appl. No.: 09/363,719

(22) Filed: Jul. 29, 1999

(30) Foreign Application Priority Data

Jul. 31, 1998 (AT) ..................................................... 1325/98

(51) Int. Cl.⁷ ....................................................... A61C 1/10
(52) U.S. Cl. ................................................. 433/84; 433/82
(58) Field of Search .................................. 433/84, 85, 82, 433/92

(56) References Cited

U.S. PATENT DOCUMENTS

| 4,213,243 | * | 7/1980 | Flatland | 433/82 |
| 4,468,217 | * | 8/1984 | Kuznick et al. | 433/92 |
| 5,464,350 | * | 11/1995 | Bierbaum | 433/84 |
| 5,474,451 | * | 12/1995 | Dalrymple et al. | 433/82 |
| 5,556,279 | * | 9/1996 | Wolf et al. | 433/82 |
| 5,716,210 | | 2/1998 | Novak . | |

FOREIGN PATENT DOCUMENTS 0591953    4/1994   (EP) .

* cited by examiner

Primary Examiner—Todd E. Manahan
(74) Attorney, Agent, or Firm—Friedrich Kueffner

(57) ABSTRACT

A filter for spray ducts of dental or surgical handpieces, wherein transfer of media from a coupling hose to the handpiece takes place through a plurality of small openings in an essentially cylindrical portion of the coupling hose of the handpiece, wherein the size of the openings determines the filtering properties. The essentially cylindrical portion has a collection duct located radially outside of the filter openings, wherein the collection duct is connected with a spray line.

7 Claims, 2 Drawing Sheets

FILTER FOR SPRAY DUCTS OF DENTAL OR SURGICAL HANDPIECES

BACKGROUND OF THE INVENTION

1. Field of the Invention

The present invention relates to a filter for spray ducts of dental or surgical handpieces.

2. Description of the Related Art

Dental or surgical handpieces have extremely thin ducts through which the spray water and/or spray air is conducted to the tip of the instrument where the medium is applied usually in the form of a spray to the work area for cooling and for removing removed tooth or bone material.

Because of the extremely small diameters of the spray ducts in the instrument, the ducts sometimes become clogged.

The most obvious solution of this problem, which is to provide an appropriate fine filter in the supply unit, is not used for various reasons. One reason is the fact that a not insignificant portion of the impurities emanate from the O-ring seals between the supply hose and the handpiece. These O-rings are subjected to shearing loads when they are mounted or when the handpieces are removed, which together with the geometry of the coupling leads to the abrasion of small rubber particles.

It must additionally be pointed out that the manufacturers of the supply units, in which also various control and regulating devices for the dental or surgical handpieces are provided, usually are not the manufacturers of the handpieces; rather, the supply units are manufactured by separate manufacturers who specialize in producing hospital and medical supplies.

However, since the users of the handpieces are to be protected as much as possible from these problems and since the repairs in the case of clogging of the lines must be carried out by the maintenance service of the manufacturers of the handpieces, there is an increasing demand for providing filters which protect the handpiece.

For example, EP 0 591 953 A provides a solution in which cylindrical filter cartridges are mounted in the area between the supply hose and the headpiece head; however, this requires a large amount of space and additionally makes it necessary to periodically replace the cartridges. Even though this activity is to be preferred over a repair, it is still an unpleasant fine-mechanical activity which has to be carried out by the physician or his or her assistant; this means that the replacement will be delayed as long as possible and the device is still operated when the filter is actually already unduly clogged and leads to a pressure drop.

Another solution is disclosed in U.S. Pat. No. 5,716,210. A filter piece is inserted between the handpiece and the supply hose, wherein the filter piece is provided with corresponding connections for the supply hose and the handpiece. This solution has the advantage that the filter piece can be easily replaced; the disadvantages are the high costs of such an intermediate filter piece and the mechanical problems which always occur when all releasable connections are doubled, and of course the fact that the filter piece is located upstream of the O-ring seals of the handpiece.

In addition, the filters themselves are so small that in many cases a large portion of their pores are clogged already after filtering out a few particles and are no longer capable of operating. This is primarily due to the fact that the filter surface must be located within the cross-section of the spray duct and, therefore, leads already in the empty state to a considerable reduction of the available cross-section.

SUMMARY OF THE INVENTION

Therefore, it is the primary object of the present invention to provide a filter which does not have the disadvantages of the previously known constructions and which can be manufactured in an advantageous manner, wherein a sufficient cross-section remains available for making possible a satisfactory spray effect even over longer periods of operation and with increasing accumulations of held-back particles. In addition, it should be possible to clean the filter according to the invention easily and without disassembling the handpiece.

In accordance with the present invention, the transfer of the media from the coupling hose to the handpiece takes place through a plurality of small openings in the essentially cylindrical portion of the coupling hose of the handpiece, wherein the size of the openings determines the filtering properties.

As a result of the measure according to the present invention, the foreign bodies which reach the coupling area through the supply hose and are to be filtered out remain stuck at the inner circumference of the handpiece where they drop off when the handpiece is removed from the supply hose and from where it may be possible to remove them by slightly tapping the handpiece.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

DESCRIPTION OF THE PREFERRED EMBODIMENTS

Figure 1:
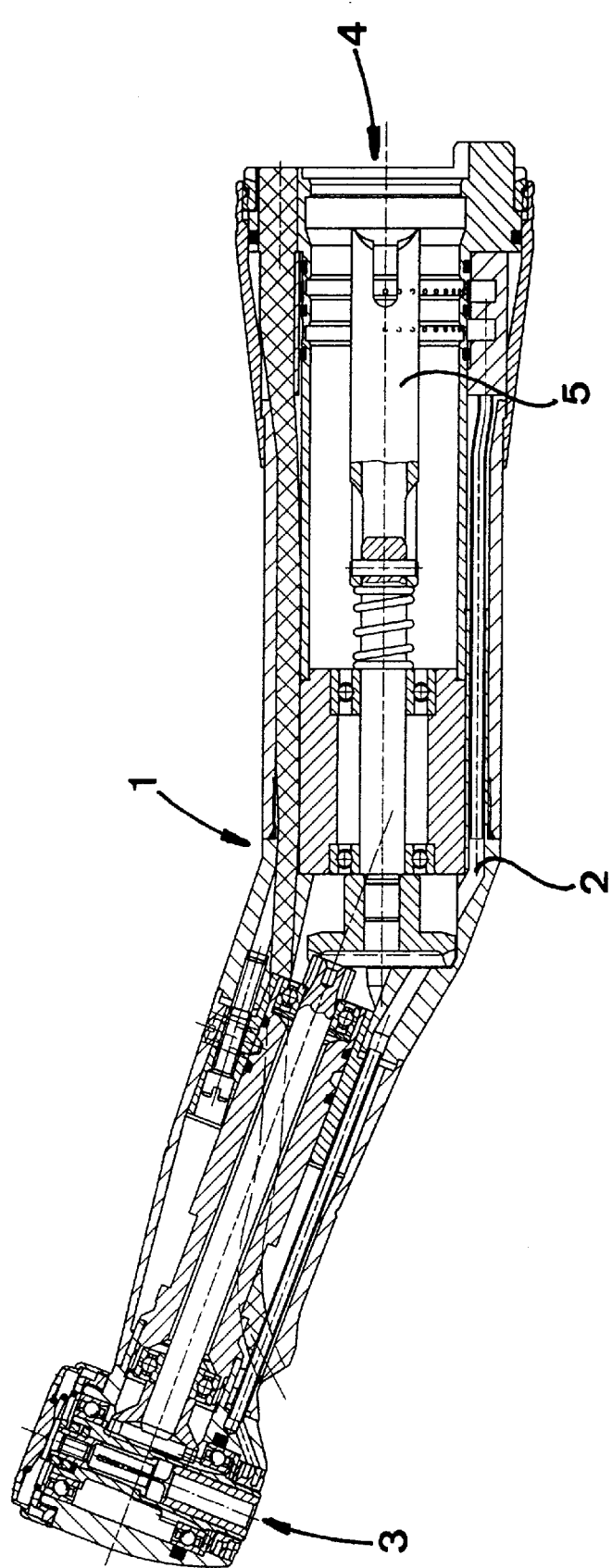
FIG. 1 is a sectional view of the handpiece according to the present invention.

The handpiece 1 illustrated in FIG. 1 of the drawing includes a spray supply line 2 for air or water. Another supply line conducting the second medium, i.e. water or air, is arranged offset in circumferential direction relative to the spray line 2 and is not illustrated. The sectional view of FIG. 1 does not extend in a plane, rather, the section is made to include the spray line 2.

Two distribution ducts arranged one above the other are provided at the head 3 of the headpiece 1. One of the distribution ducts is supplied with the appropriate medium by the spray line 2, while the other distribution duct is supplied by the spray line which is not shown. The lower distribution duct is open by means of nozzles toward the outside, wherein the nozzles are constructed in such a way that they direct a spray of water and air to the work location. The spray is formed as a result of the fact that the two distribution ducts are also in communication with each other through openings, so that when the two media flow through the two distribution ducts and finally through the outwardly directed nozzles, the desired spray is formed.

This manner of forming the spray is known in the art and, as mentioned above, frequently leads to clogging in the distribution ducts or the nozzles or the connecting ducts between the distribution ducts because this is where all of the spray ducts have the smallest cross-sections. It is readily apparent that repairs of these areas of the instrument are complicated and expensive and can certainly not be carried out in a dentist's office or in a hospital; rather, it is necessary to ship the device to a service location.

The solution of the above-described problem according to the present invention is provided at the other end of the handpiece 1, i.e., at the coupling end 4. The end of the supply hose to be connected to the instrument is inserted into the opening of the handpiece 1, wherein the coupling piece of the supply hose is provided at appropriate locations with a drive, a light source and means for supplying the spray air and the spray water. Other media, for example, electric energy, can also be supplied, however, this does not concern the present invention.

Other types of couplings can also be provided in which, for example, instead of the mechanical drive energy for the shaft 5 of the handpiece 1, electricity is supplied to the appropriate handpiece for a micro-motor or compressed air is supplied for a turbine. This also does not usually impair the configuration of the present invention and any problems occurring with respect to space can be easily circumvented or eliminated by those skilled in the art of manufacturing handpieces who are informed of the invention.

Figure 2:
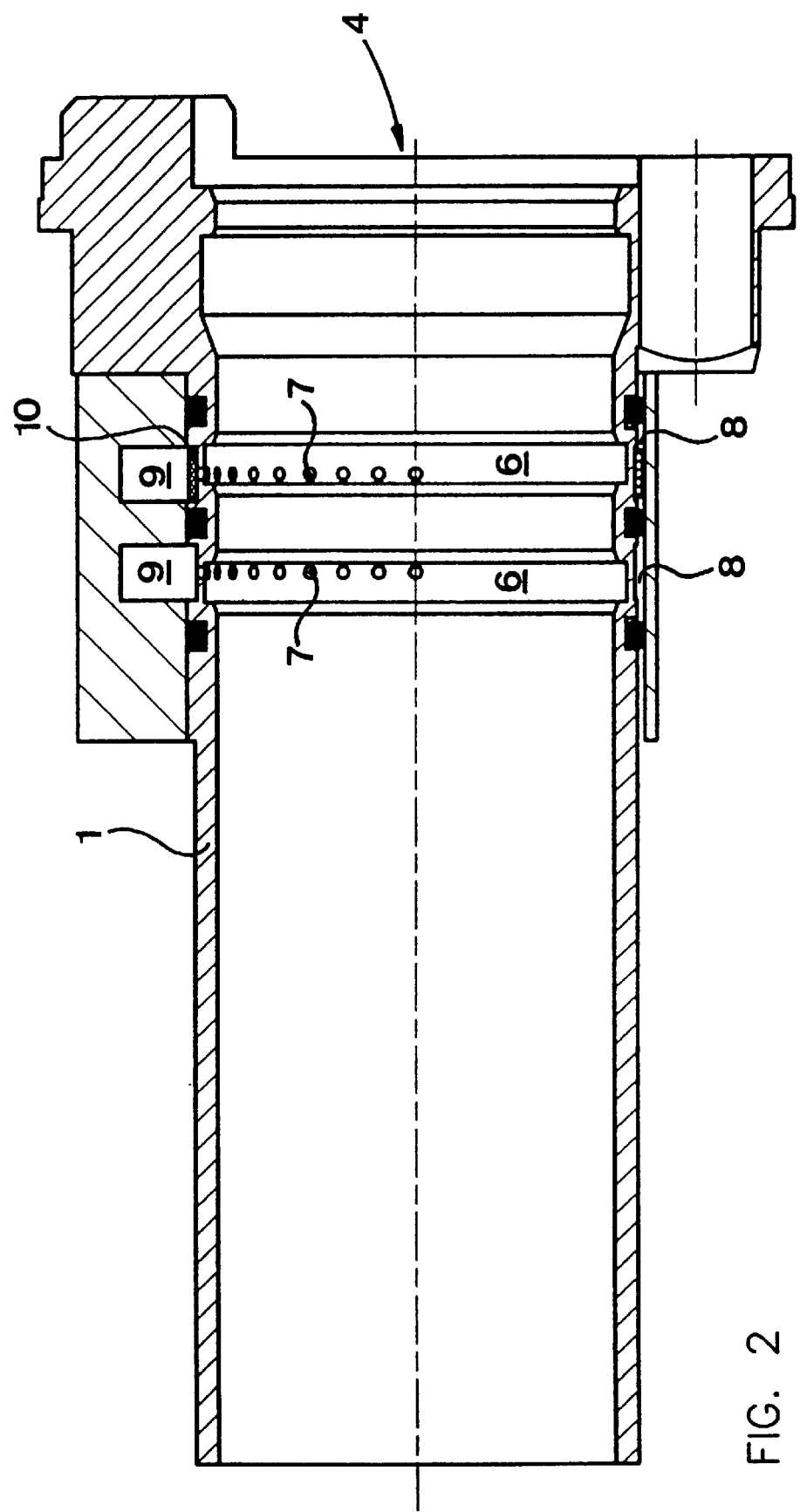
FIG. 2 is a sectional view, on a larger scale, showing a detail of the handpiece of FIG. 1.

The features according to the present invention can best be seen in FIG. 2. The illustrated end of the handpiece 1 on the side of the coupling is provided with at least one annular groove 6 in the axial area of the transfer of a spray medium. A plurality of filter openings 7 are provided in the groove bottom, wherein a few of the filter openings 7 are schematically illustrated in FIG. 2. After passing through these filter openings 7, the respective spray medium is located in another annular duct or collection duct 8 in which the spray medium is collected and supplied through a discharge space 9 to the actual spray line 2 shown in FIG. 1.

It is readily apparent that with increasing clogging of filter openings 7, by removing the handpiece 1 from the supply hose as it is illustrated in FIGS. 1 and 2, the impurities can be easily removed by slightly tapping the handpiece or by brushing it with a soft brush, without requiring specific knowledge or devices.

FIG. 2 shows a further development of the invention in the spray duct on the right hand side as seen in FIG. 2. A flat rubber ring 10 loosely rests against the outer side of the annular groove 6 and is lifted by the spray medium which is conducted radially from the inside toward the outside, so that the spray medium can flow to the discharge space 9 and from there into the actual spray duct 2.

When the motor is switched off, return suction effects, as they are known from turbines and motors of handpieces, also occur in the spray ducts and contaminated materials, such as blood, saliva and abrasions, are also drawn into the spray ducts and pose the danger of infections for the next patient. Even though this danger is small in the spray duct because of the small dimensions of the nozzles in the handpiece head 3, this danger is not negligible, as already recognized in the prior art references.

In this connection, reference is made to EP 0 230 010 B which in FIG. 12 shows similar measures, wherein, however, an O-ring is used which is not well suitable for this purpose because of its poor expandability and which would completely fail because of the presence of many openings 7 according to the present invention.

The invention is not limited to the illustrated embodiment but can be modified in various ways. For example, it is possible to select openings which are not circular and to select the dimensions of the openings in dependence on the desired filtering effect.

It is also possible to achieve filtering effects as they are mentioned as an object, for example, in the above-discussed references, in accordance with which even impurities of molecular size are to be held back. In that case, it is possible to use outside or instead of the flat rubber ring 10 an annular filter which, because of the prefiltering effect of the filter openings 7 and the large available surface area, have a significantly longer service life than the previously known filter cartridges or filter discs.

An additional advantage is the fact that the mechanical stability of the handpiece and of the connection between the handpiece and the coupling does not suffer and that the external dimensions of the handpiece remain unchanged.

The dimensions of the annular grooves 6 do not have to have the proportions illustrated in the drawing; rather, the grooves 6 can also be wider or narrower; it is only necessary to take into consideration the usually predetermined dimensions of the coupling piece on the side of the hose.

As compared to the conventional O-ring provided for this purpose, the flat rubber ring 10 used in accordance with the present invention has the advantage that it rests with a lower force against the periphery and can be lifted more easily; this is due to the fact that the rubber ring 10 has on the outer side of the groove a large surface area. An easily expandable embodiment of the flat rubber ring 10 can also be used, so that the rubber ring can be lifted off more easily than the previously known O-ring.

While specific embodiments of the invention have been shown and described in detail to illustrate the inventive principles, it will be understood that the invention may be embodied otherwise without departing from such principles.

I claim:

1. A filter for a spray duct of a dental or surgical handpiece, wherein the handpiece has a coupling pipe with an essentially cylindrical portion, wherein the filter is comprised of a plurality of small filter openings in the essentially cylindrical portion for effecting a media transfer from a coupling hose to the handpiece.

2. The filter according to claim 1, wherein the essentially cylindrical portion has a collection duct located radially outside of the filter openings, wherein the collection duct is connected with a spray line.

3. The filter according to claim 2, wherein the essentially cylindrical portion has a discharge space in communication with the collection duct and with the spray line.

4. The filter according to claim 1, wherein the essentially cylindrical portion of the coupling pipe has at least one annular groove and the at least one annular groove has an outer surface, further comprising an elastic annularly closed flat strip on the outer surface.

5. The filter according to claim 4, wherein the flat strip is a flat rubber ring.

6. The filter according to claim 2, wherein a fine filter is mounted downstream of the filter openings.

7. The filter according to claim 6, wherein the fine filter is mounted at the collection duct.

* * * * *